(12) United States Patent
Fowler et al.

(10) Patent No.: US 9,173,687 B2
(45) Date of Patent: Nov. 3, 2015

(54) FULCRUM CAP FOR SPINAL CONSTRUCTS

(71) Applicant: DePuy Synthes Products, LLC, Raynham, MA (US)

(72) Inventors: Mary Louise Fowler, Bexley, OH (US); Thomas J. Runco, Canton, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 161 days.

(21) Appl. No.: 13/834,676

(22) Filed: Mar. 15, 2013

(65) Prior Publication Data

US 2014/0277151 A1    Sep. 18, 2014

(51) Int. Cl.
*A61B 17/58* (2006.01)
*A61B 17/60* (2006.01)
*A61B 17/70* (2006.01)

(52) U.S. Cl.
CPC ........... *A61B 17/7074* (2013.01); *A61B 17/708* (2013.01); *A61B 17/7077* (2013.01)

(58) Field of Classification Search
CPC .................................. A61B 17/7074–17/708
USPC ........... 403/79, 142, 157, 385, 396, 398–399; 606/86 A, 90, 99, 104, 105, 86 B, 265
See application file for complete search history.

(56) References Cited

U.S. PATENT DOCUMENTS

| | | | | |
|---|---|---|---|---|
| 4,619,282 A * | 10/1986 | Battiston | ........................ | 135/67 |
| 5,531,751 A * | 7/1996 | Schultheiss et al. | ............ | 606/96 |
| 6,065,899 A * | 5/2000 | Adams et al. | ................ | 403/397 |
| 6,090,113 A * | 7/2000 | Le Couedic et al. | .......... | 606/914 |
| 6,116,810 A * | 9/2000 | Eberle | ............................ | 403/391 |
| 6,523,231 B1 * | 2/2003 | Lassiter | .......................... | 24/339 |
| 7,686,814 B2 * | 3/2010 | Lim et al. | ...................... | 606/105 |
| 7,886,406 B2 * | 2/2011 | Chang | .............................. | 16/252 |
| 7,918,792 B2 * | 4/2011 | Drzyzga et al. | ............... | 600/215 |
| 7,985,242 B2 * | 7/2011 | Forton et al. | ................... | 606/246 |
| 8,007,516 B2 * | 8/2011 | Chao et al. | ...................... | 606/246 |
| 8,177,817 B2 * | 5/2012 | Fallin | ............................ | 606/278 |
| 8,262,662 B2 * | 9/2012 | Beardsley et al. | ........... | 606/86 A |
| 8,414,588 B2 * | 4/2013 | Stad et al. | .................... | 606/86 A |
| 8,444,649 B2 * | 5/2013 | Stad et al. | .................... | 606/86 A |
| 8,491,590 B2 * | 7/2013 | Stad et al. | ........................ | 606/90 |
| 8,523,876 B2 * | 9/2013 | Lim et al. | ...................... | 606/105 |
| 8,608,746 B2 * | 12/2013 | Kolb et al. | .................... | 606/86 A |
| 8,894,648 B2 * | 11/2014 | Dominik et al. | ................ | 606/57 |

(Continued)

OTHER PUBLICATIONS

[No Author Listed] Surgical Technique Guide. Expedium: Vertebral Body Derotation. DePuy Spine, Inc. Sep. 2011. 14 pages.

*Primary Examiner* — Eduardo C Robert
*Assistant Examiner* — Jacqueline Johanas
(74) *Attorney, Agent, or Firm* — Nutter McClennen & Fish LLP (57) ABSTRACT

Systems and methods for manipulating a spinal construct are provided herein. In general, the system includes first and second sleeves extending from vertebrae and a fulcrum that can be releasably coupled to the sleeves. In certain aspects, the fulcrum can receive a portion of the sleeves therein and can allow the sleeves to pivot about the fulcrum in response to an applied force. The fulcrum can releasably couple to the sleeves in a variety of ways, and a position of the fulcrum relative to the sleeves can vary depending on whether there is an applied distracting, compressing, and/or derotating force. In some embodiments, user can manipulate the first and second sleeves relative to the fulcrum, using one hand, to distract, compress, and/or derotate the vertebrae.

17 Claims, 11 Drawing Sheets

(56) References Cited

U.S. PATENT DOCUMENTS

| | | | |
|---|---|---|---|
| 8,894,655 B2* | 11/2014 | Fallin et al. | 606/86 A |
| 2003/0060826 A1* | 3/2003 | Foley et al. | 606/61 |
| 2004/0143265 A1* | 7/2004 | Landry et al. | 606/61 |
| 2004/0176763 A1* | 9/2004 | Foley et al. | 606/60 |
| 2005/0234449 A1* | 10/2005 | Aferzon | 606/61 |
| 2005/0245928 A1* | 11/2005 | Colleran et al. | 606/61 |
| 2005/0273132 A1* | 12/2005 | Shluzas et al. | 606/198 |
| 2006/0009777 A1* | 1/2006 | Lim et al. | 606/90 |
| 2006/0264934 A1* | 11/2006 | Fallin | 606/61 |
| 2007/0021835 A1* | 1/2007 | Edidin | 623/17.12 |
| 2007/0288026 A1* | 12/2007 | Shluzas | 606/73 |
| 2008/0077138 A1* | 3/2008 | Cohen et al. | 606/61 |
| 2008/0119860 A1* | 5/2008 | McCarthy | 606/87 |
| 2009/0062858 A1* | 3/2009 | Dziedzic et al. | 606/278 |
| 2009/0228053 A1* | 9/2009 | Kolb et al. | 606/86 A |
| 2010/0004695 A1* | 1/2010 | Stad et al. | 606/86 A |
| 2010/0036443 A1* | 2/2010 | Hutton et al. | 606/86 R |
| 2010/0292704 A1* | 11/2010 | Stoffel et al. | 606/99 |
| 2010/0331901 A1* | 12/2010 | Iott et al. | 606/86 A |
| 2012/0089191 A1* | 4/2012 | Altarac et al. | 606/279 |
| 2012/0123477 A1* | 5/2012 | Landry et al. | 606/264 |
| 2012/0197302 A1* | 8/2012 | Fallin | 606/279 |
| 2013/0018423 A1 | 1/2013 | Stad et al. | |
| 2013/0184763 A1* | 7/2013 | McClintock et al. | 606/279 |
| 2014/0074171 A1* | 3/2014 | Hutton et al. | 606/279 |
| 2014/0128924 A1* | 5/2014 | Perrow et al. | 606/287 |
| 2014/0277168 A1* | 9/2014 | Hutton et al. | 606/279 |

* cited by examiner

A # FULCRUM CAP FOR SPINAL CONSTRUCTS

FIELD

Methods and devices for use in spinal surgery are disclosed herein and, in particular, methods and devices for manipulating one or more bone anchors inserted in a patient's spine.

BACKGROUND

For a number of known reasons, spinal fixation devices are used in orthopedic surgery to align and/or fix a desired relationship between adjacent vertebral bodies. Such devices typically include a spinal connector, such as a relatively rigid fixation rod, that is coupled to adjacent vertebrae by attaching the connector to various anchoring devices, such as hooks, bolts, wires, or screws. The connector may have a predetermined contour that has been designed according to the properties of the target implantation site, and once installed, the instrument holds the vertebrae in a desired spatial relationship, either until healing or spinal fusion has taken place, or for some longer period of time.

Spinal connectors can be anchored to specific portions of the vertebrae. Since each vertebra varies in shape and size, a variety of anchoring devices have been developed to facilitate engagement of a particular portion of the bone. Pedicle screw assemblies, for example, have a shape and size that is designed and configured to engage pedicle bone. Such screws typically include a threaded shank that is adapted to be threaded into a vertebra, and a head portion having a receiving element, usually in the form of a U-shaped head. A set-screw, plug, or similar type of fastening mechanism is used to lock the spinal connector, e.g., a spinal rod, into the receiving head of the pedicle screw. In use, the shank portion of each screw is threaded into a vertebra, and once properly positioned, a rod is seated through the receiving member of each screw. The rod is locked in place by tightening a cap or other fastener mechanism to securely interconnect each screw and the spinal rod.

Minimally-invasive devices and methods for implanting spinal fixation devices are advantageous because such devices and methods utilize fewer and/or smaller incisions for introducing and implanting anchoring devices and spinal connectors at a target site within a patient's spine. Such procedures offer advantages over invasive techniques because they reduce the amount of damage to surrounding tissue and muscle and the amount of time required to complete the procedure. During minimally invasive surgery (MIS), percutaneous extensions are often mated to or formed on a bone anchor. The extensions can be used for guiding tools and devices to the implant site and, once the bone anchor is implanted, the extensions can be manipulated from outside of the patient's body to distract or compress vertebrae. However, these manipulation steps can be cumbersome as the working area tends to be crowded and the required instrumentation can be difficult to position, adjust, and/or maintain at a desired location. The size and configuration of the extensions can also make it difficult to achieve the desired compression or distraction, particularly when the extensions intersect and are criss-crossed.

Accordingly, there is a need for improved methods and devices for manipulating one or more bone anchors implanted in a patient's spine.

SUMMARY

Various devices and methods for distracting, compressing, and/or derotating vertebrae are provided herein. In some embodiments, a spinal instrumentation kit includes a first bone anchor configured to be implanted in a first vertebra and a second bone anchor configured to be implanted in a second vertebra. A first elongate body can be configured to couple to the first bone anchor, the first elongate body having an inner lumen extending therethrough for providing a pathway through tissue to the first bone anchor. A second elongate body can be configured to couple to the second bone anchor, the second elongate body having an inner lumen extending therethrough for providing a pathway through tissue to the second bone anchor. The kit can further include a connector configured to couple to a proximal portion of the first and second elongate bodies such that, when the first and second bone anchors are implanted in first and second vertebra and the first and second elongate bodies are coupled to the first and second bone anchors, the connector is configured to function as a fulcrum to allow pivotal movement of the first and second elongate bodies about the fulcrum to thereby compress or distract the first and second vertebrae relative to one another.

The connector can have various features for coupling to the elongate bodies. The connector can be configured to slide along the length of the first elongate body. The connector can include a cap portion configured to receive a proximal end of the first elongate body therein. The connector can include a ring-shaped clamp configured to be positioned around the first and second elongate bodies. The connector can include a ring-shaped member configured to be slidably disposed around one of the first and second elongate bodies, and at least one support arm extending outward from the ring-shaped member and configured to seat the other one of the first and second elongate bodies.

In some embodiments, the connector can include a ring-shaped member configured to be slidably disposed around one of the first and second elongate bodies, the ring-shaped member having a U-shaped extension and first and second support arms extending therefrom. The U-shaped extension and the first and second support arms each can be configured to seat the other one of the first and second elongate bodies. The connector can include a cylindrical portion having a first height and a hemi-cylindrical portion extending from the cylindrical portion, the hemi-cylindrical portion having a second height that is greater than the first height. In some embodiments, the connector includes an adjustable rack configured to adjust the distance between a portion of the connector that couples to the first elongate body and a portion of the connector that couples to the second elongate body. In some embodiments, the ring-shaped member is configured to prevent an elongate body received therein from rotating relative to the connector.

In some embodiments, the first and second elongate bodies include first and second sleeves, each of the first and second sleeves having an inner lumen extending therethrough for providing a pathway through tissue.

A medical device connector is also provided, and includes a ring member configured to be disposed around a proximal portion of a first elongate body and an extension coupled to a first side of the ring member and configured to engage a proximal portion of a second elongate body to thereby couple the second elongate body to the first elongate body.

In some embodiments, the medical device connector can further include a wing member coupled to a second, opposite side of the ring member, the wing member extending laterally outward from the ring member. In other embodiments, the extension can be substantially U-shaped. In still other embodiments, the extension can be substantially oval-shaped.

Methods for spinal distraction or compression are also provided herein. In some embodiments, a method can include coupling a connector to a proximal portion of a first elongate body and a second elongate body such that the connector forms a fulcrum. The first elongate body can extend through tissue and have a distal end coupled to a first bone anchor implanted in a first vertebra, and the second elongate body can extend through tissue and have a distal end coupled to a second bone anchor implanted in a second vertebra. The method can include manipulating the first and second elongate bodies to pivot the elongate bodies about the fulcrum provided by the connector, thereby compressing or distracting the first and second vertebrae relative to one another.

The method can include moving first and second elongate bodies toward and away from one another. For example, manipulating the first and second elongate bodies can include squeezing the first and second elongate bodies towards one another at a location adjacent to a surface of the tissue to compress the first and second vertebrae. As another example, manipulating the first and second elongate bodies can include applying a spreading force to the first and second elongate bodies apart at a location adjacent to a surface of the tissue to distract the first and second vertebrae. In some embodiments, the first and second elongate bodies can be sleeves.

The present invention further provides devices, systems, and methods as claimed.

BRIEF DESCRIPTION OF THE DRAWINGS

The invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention Further, in the present disclosure, like-numbered components of the embodiments generally have similar features, and thus within a particular embodiment each feature of each like-numbered component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

A person skilled in the art will appreciate that the methods and devices disclosed herein have application in conventional minimally-invasive and open surgical instrumentation as well as application in robotic-assisted surgery.

Figure 1:
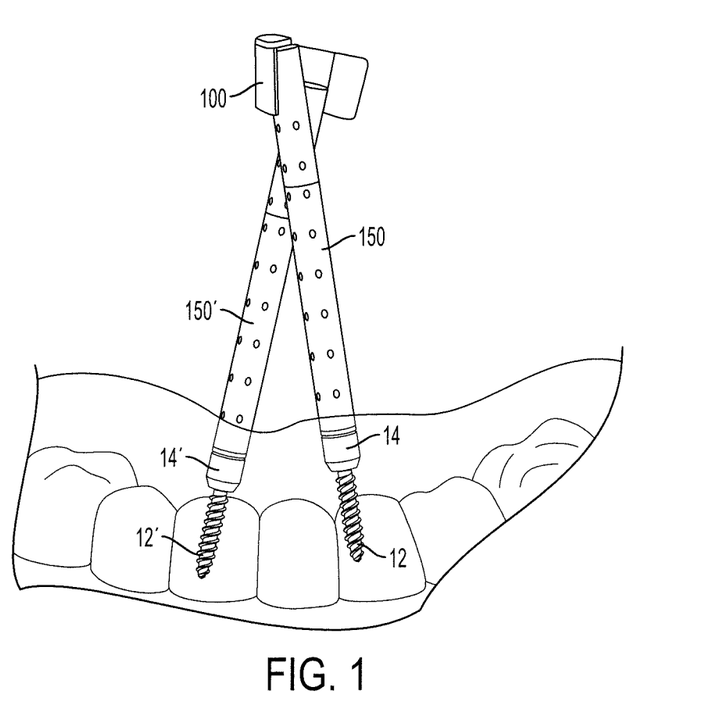
FIG. 1 is a perspective view of two bone anchor assemblies extending from adjacent vertebrae and being coupled to a fulcrum cap according to one embodiment.

Various systems and methods for manipulating a spinal construct are provided herein. In general, a fulcrum cap or "connector" is provided for use with at least two spinal anchor extensions, sometimes referred to herein as elongate bodies and more specifically, as sleeves. By way of non-limiting example, FIG. 1 illustrates a fulcrum cap 100 and first and second sleeves 150, 150'. Each sleeve 150, 150' is coupled to or formed on a spinal anchor, such as a pedicle screw having a rod-receiving portion 14, 14' for seating a spinal fixation element (e.g., a spinal fixation rod) and a shank 12, 12' that is implanted in a vertebra. As shown, the fulcrum cap 100 can mate to or otherwise seat a portion of each sleeve 150, 150' to allow the sleeves to pivot about the fulcrum in response to an applied force. As a result, the fulcrum cap 100 can provide an increased mechanical advantage for assisting with distraction, compression, derotation, or other manipulating of the vertebrae. Manipulation forces can be applied directly to the sleeves and/or to one or more instruments inserted therethrough.

A person skilled in the art will appreciate that the sleeves and the bone anchors can have a variety of configurations, exemplary embodiments of which will be discussed in more detail below. By way of non-limiting example, the sleeves can be in the form of extensions that are integrally formed on the bone anchors and that can be frangibly detached therefrom during use, or the extensions can be separate members that mate to or that can be positioned adjacent to the bone anchors. Various bone anchors can also be used, including monoaxial and polyaxial spinal screws, hooks, etc.

Figure 2A:
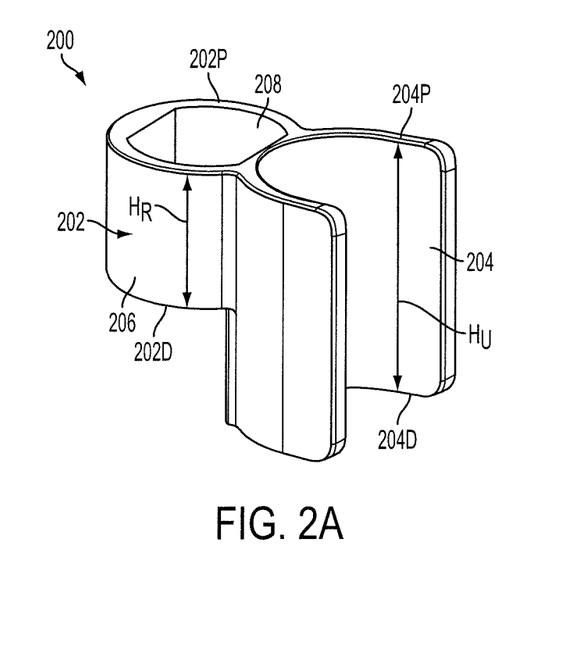
FIG. 2A is a perspective view of one embodiment of a fulcrum cap.
Figure 2B:
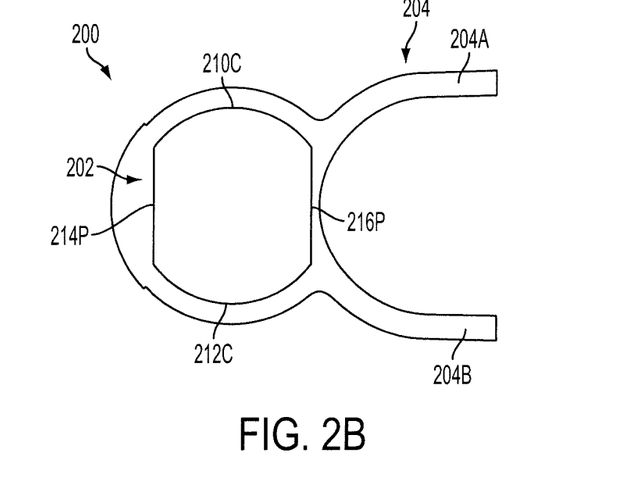
FIG. 2B is a top view of the fulcrum cap of FIG. 2A.

A first embodiment of a fulcrum cap 200 is shown in FIGS. 2A and 2B, and includes a ring-shaped member 202 and a U-shaped, hemi-cylindrical extension 204. The ring-shaped member 202 can be configured to mate to a proximal portion of a first sleeve, and the U-shaped extension 204 can be configured to seat a proximal portion of a second sleeve. While the illustrated cap 200 includes a single ring-shaped member 202 and a single U-shaped extension 204, a person skilled in the art will appreciate that the cap 200 can include any number of ring-shaped members and any number of U-shaped extensions for coupling to any number of sleeves.

In the embodiment shown in FIGS. 2A and 2B, the ring-shaped member 202 generally includes an outer surface 206 having a generally elliptical shape, an inner surface 208, a proximal surface 202P, and a distal surface 202D. The particular shape of the inner surface 208 can vary, but in an exemplary embodiment the inner surface 208 is configured to seat and engage a proximal end of a sleeve. The inner surface 208 can thus have a shape that complements a shape of a proximal end of a sleeve. As shown in FIG. 2B, the inner surface 208 of the ring-shaped member 202 has first and second opposed curved walls 210C, 212C, and first and second opposed planar walls 214P, 216P. As will be discussed in more detail below, a sleeve can be provided having a similar shape with opposed curved walls and opposed planar walls such that the sleeve can be received within the fulcrum cap 200. The distance between each of the opposed walls can also vary, but in an exemplary embodiment the walls are sized so as to form an interference fit with a sleeve seated therein. Thus, the ring-shaped member and the sleeve seated therein can be non-rotatably coupled together.

The ring-shaped member 202 can also have a height $H_R$ that varies, but that is sufficient to allow secure mating with a sleeve. In one embodiment, the height can be in the range of about 10 mm to about 20 mm. The proximal and distal surfaces 202P, 202D can extend generally parallel to one another as shown, or in other embodiments the surfaces can be angled relative to one another or relative to the U-shaped extension 204.

The U-shaped extension 204 can also have a variety of features. In the illustrated embodiment, the U-shaped extension 204 has first and second curved support arms 204A, 204B extending outward from the outer sidewall of the ring-shaped member 202. As shown, the arms 204A, 204B can extend in a direction that is generally perpendicular to the second planar wall 216P of the ring-shaped member 202. However, a person skilled in the art will appreciate that the first and second curved arms 204A, 204B can extend from other parts of the ring-shaped member 202, or in other directions with respect to the ring-shaped member 202. A height $H_U$ of the first and second curved arms 204A, 204B can vary, but as shown in the illustrated embodiment, the height $H_U$ of the arms 204A, 204B can be greater than the height $H_R$ of the ring-shaped member 202. As shown in FIG. 2A, the proximal surface 204P of the U-shaped extension 204 and the proximal surface 202P of ring-shaped member 202 can each be planar and, in some embodiments, can be coplanar with one another. Other configurations are also possible, as will be appreciated by a person skilled in the art. In use, a first sleeve can be mated or coupled to the ring-shaped member 202 and a second sleeve can be mated or coupled to, or seated against, the U-shaped extension 204 such that the cap 200 acts as a fulcrum for manipulation forces applied to the sleeves or instruments inserted therethrough.

The ring-shaped member 202 and the U-shaped extension 204 can be integrally formed as shown (e.g., via injection molding), or can be provided as separate components selectively or permanently coupled to one another. Any of a variety of materials can be used to form the fulcrum cap 200, including titanium, titanium alloys, stainless steel, cobalt chrome, PEEK, high-strength polymers, and/or combinations thereof.

Figure 3A:
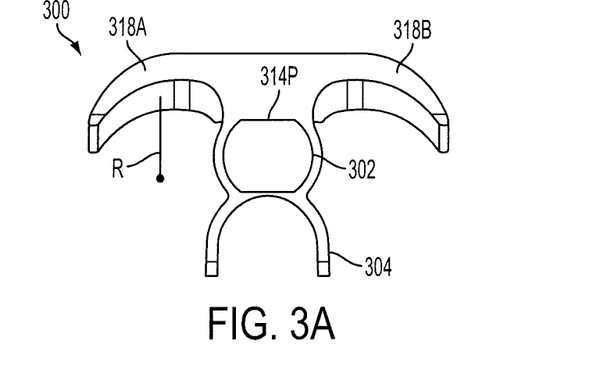
FIG. 3A is a top view of another embodiment of a fulcrum cap that includes a plurality of wings.
Figure 3B:
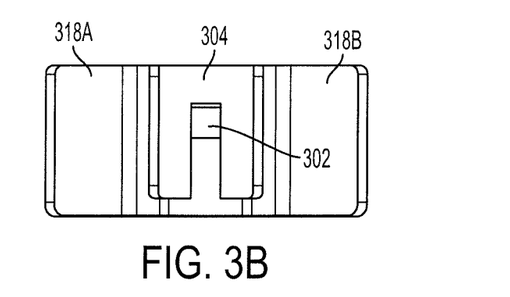
FIG. 3B is a side view of the fulcrum cap of FIG. 3A.
Figure 3C:
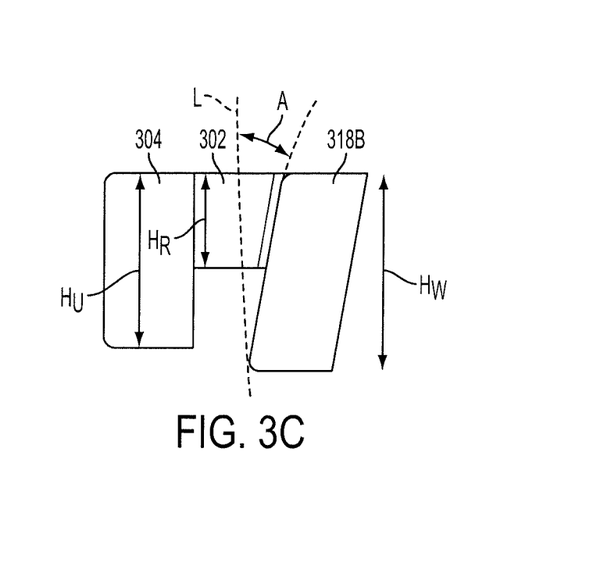
FIG. 3C is a side view of the fulcrum cap of FIG. 3B rotated 90° about a central longitudinal axis thereof.

FIGS. 3A-3C illustrate another exemplary embodiment of a fulcrum cap 300 that includes a ring-shaped member 302 and a U-shaped extension 304, which can have the same structure and function as the ring-shaped member 202 and the U-shaped extension 204 described above. The fulcrum cap 300 also includes one or more wings 318A, 318B configured to seat, mate, or couple to one or more respective sleeves. The first and second wings 318A, 318B can extend from a side of the ring-shaped member 302 opposite to the U-shaped extension 304 (e.g., adjacent to the first planar wall 314P of the ring-shaped member 302). The wings 318A, 318B can have a curved or arcuate shape, and can have a thickness that decreases towards the lateral extremes of the wings, such that the wings are tapered. The first and second wings 318A, 318B can define curved sleeve-engaging surfaces having a radius R. It will be appreciated that the radius R can be selected based on a variety of factors, including the size and shape of the sleeves with which the fulcrum cap 300 is to be used. In some embodiments, the radius R can be in the range of about 9 mm to about 20 mm, or in the range about 75% to about 200% of an outer diameter of the sleeve. As shown in FIG. 3C, the wings 318A, 318B can have a height $H_W$ that can be greater than the height $H_R$ of the ring-shaped member 302 and the height $H_U$ of the U-shaped extension 304. In some embodiments, the wings 318A, 318B can have longitudinal axes which are not parallel to the central longitudinal axis L of the ring-shaped member 302. In particular, as shown in FIG. 3C, the first and second wings 318A, 318B can extend at an angle A relative to the central longitudinal axis L of the ring-shaped member 302. The wings 318A, 318B can be formed integrally with the ring-shaped member 302 and/or the U-shaped extension 304, or can be selectively or permanently attached thereto.

In use, the fulcrum cap 300 can be configured to mate or couple to a plurality of sleeves. In particular, any one or more of the ring-shaped member 302, the U-shaped extension 304, and the wings 318A, 318B can be configured to receive a respective sleeve. When mated to one or more sleeves, the cap 300 can act as a fulcrum for manipulation forces applied to the sleeves or instruments inserted therethrough.

Figure 4:
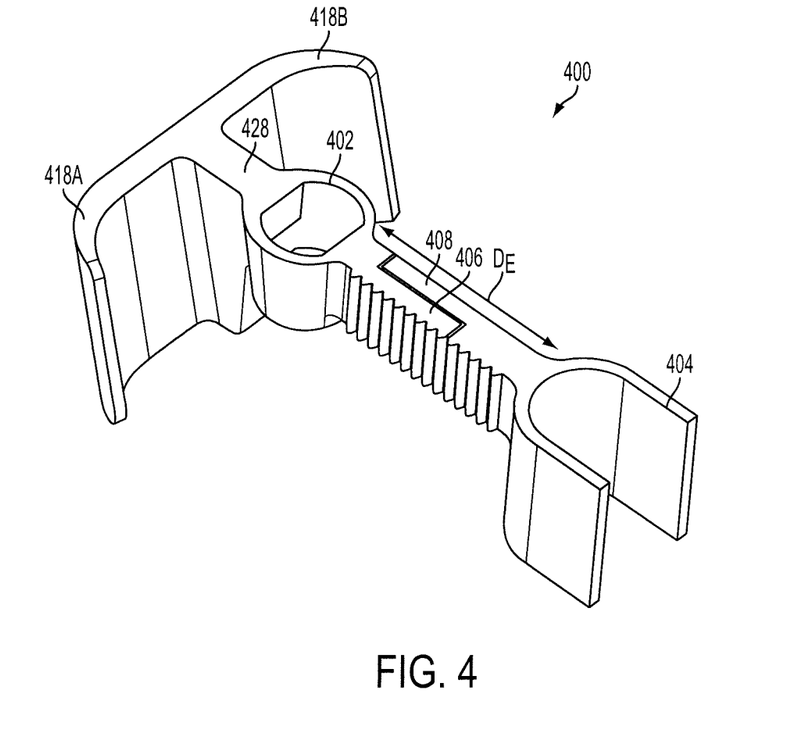
FIG. 4 is a perspective view of another embodiment of a fulcrum cap having a cap portion and an extension that are adjustable toward and away from one another.

FIG. 4 illustrates another exemplary embodiment of a fulcrum cap 400 that includes a ring-shaped member 402, a U-shaped extension 404 spaced apart from the ring-shaped member 402, and wings 418A, 418B that extend on either side of the ring-shaped member 402. As shown, the ring-shaped member 402 can have a first rack 406 and the U-shaped extension 404 can have a second rack 408. The first and second racks 406, 408 can have corresponding mating features (not shown), such as ratchet teeth, that are of complementary shapes and sizes such that the first and second racks 406, 408 can interlock when the ring-shaped member 402 and the U-shaped extension 404 are in a first, retracted position, as shown in FIG. 4. The ring-shaped member 402 and the U-shaped extension 404 can be movable or extendable from the first, retracted position to a second, extended position (not shown) to increase a distance $D_E$ between the ring-shaped member 402 and the U-shaped extension 404. Although not shown, a person of skill in the art will appreciate that any one of a variety of types of locking members can be used to maintain the fulcrum cap in a position with desired spacing between ring-shaped member 402 and U-shaped extension 404. In use, this can allow the fulcrum cap 400 to have an adjustable size so as to mate with first and second sleeves that are spaced apart by variable distances, such as those that extend across two or more levels of a patient's spine. It will be appreciated that various other mechanisms known in the art can be used to increase a distance between the ring-shaped member and the extension. Additionally, although the extension 404 is shown as being substantially U-shaped, a person of skill in the art will appreciate that a variety of other shapes are suitable. For example, in another embodiment the extension 404 can be substantially oval-shaped.

Figure 5:
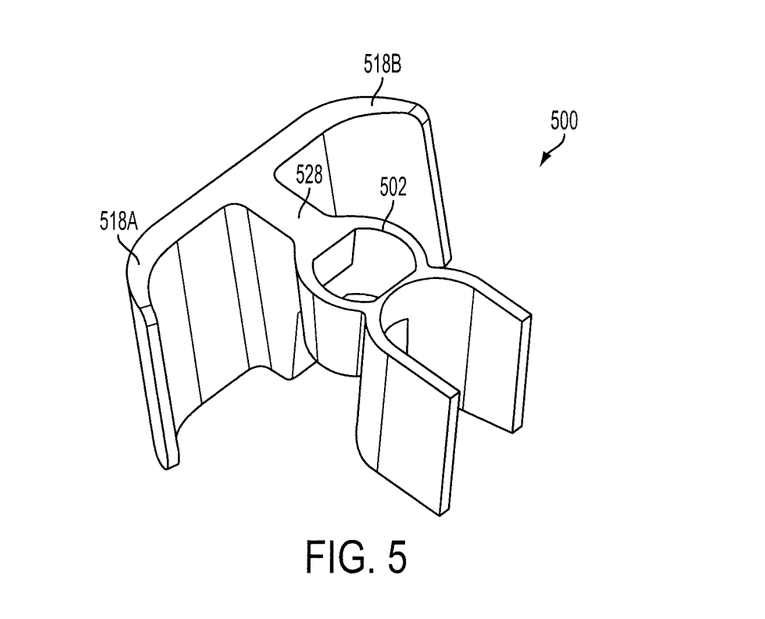
FIG. 5 is a perspective view of an embodiment of a fulcrum cap having an extension wall for spacing wing portions of the cap from a ring-shaped portion of the cap.

FIG. 5 illustrates another exemplary embodiment of a fulcrum cap 500. The fulcrum cap 500 is identical to the fulcrum cap 300 described above, except that the wings 518A, 518B of the fulcrum cap 500 are spaced apart from the ring-shaped member 502 by an extension wall 528, such that the wings 518A, 518B form a substantially T-shaped structure. The extension wall 528 can advantageously provide additional clearance within the curved sleeve-receiving portions of the wings 518A, 518B, e.g., to accommodate larger-diameter sleeves.

Figure 6:
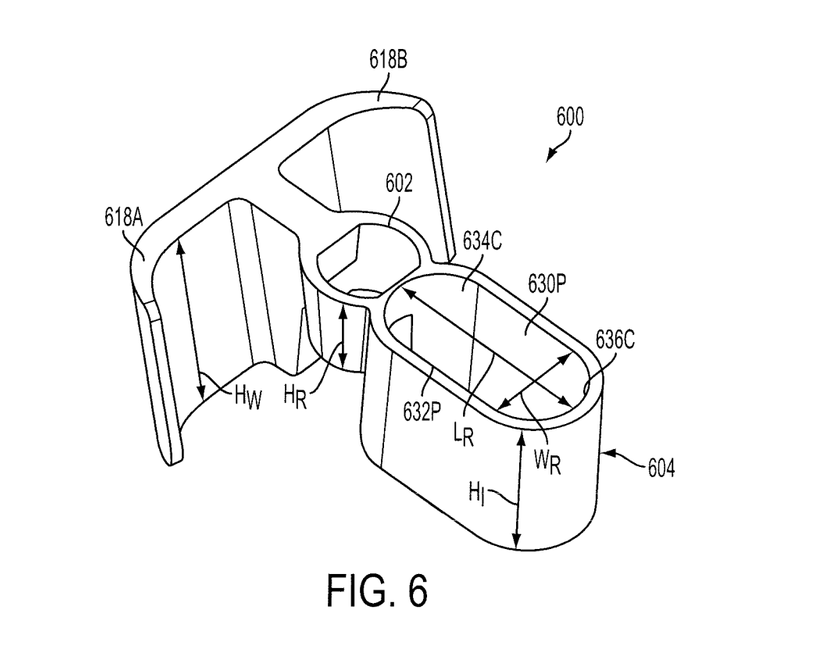
FIG. 6 is a perspective view of a fulcrum cap having a closed receiver for movably receiving a sleeve therein.

FIG. 6 illustrates another exemplary embodiment of a fulcrum cap 600. The fulcrum cap 600 is identical to the fulcrum cap 500 described above, except that the fulcrum cap 600 includes a closed receiver 604 instead of the U-shaped extension described above. The receiver 604 can define a lumen configured to receive a proximal end of a sleeve therein. The lumen can be substantially oval-shaped, and can include first and second opposed, planar sides 630P, 632P and first and second opposed, curved sides 634C, 636C. The lumen can have an inner width $W_R$ between the planar sides 630P, 632P in the range of about 15 mm to about 17 mm, and/or an inner length $L_R$ between the first and second curved sides 634C, 636C in the range of about 18 mm to about 30 mm. In some embodiments, the inner width $W_R$ of the lumen can be substantially equal to an outer diameter of a sleeve with which the fulcrum cap 600 is to be used. The lumen can thus have a size and a shape that allows the proximal end of the sleeve to move therein, e.g., toward and/or away from the first and second curved sides 634C, 636C in a single plane of motion. The receiver can have a height $H_1$ that can be greater than or less than the height $H_R$ of the ring-shaped member 602 and the height $H_W$ of the wings 618A, 618B.

Figure 7:
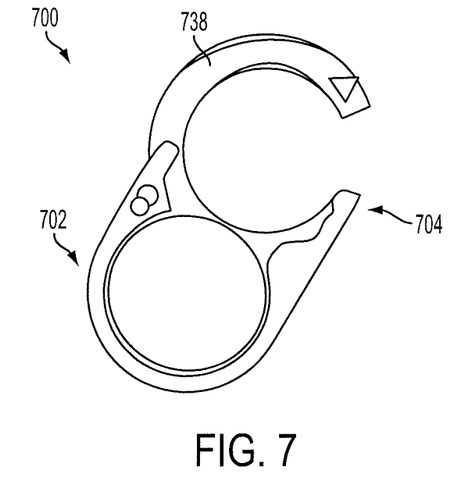
FIG. 7 is a top view of one embodiment of a fulcrum cap having a movable C-shaped jaw.

FIG. 7 illustrates another exemplary embodiment of a fulcrum cap 700. The fulcrum cap 700 includes a ring-shaped portion 702 and a clamp portion 704. The clamp portion 704 can include a hinged or pivotable C-shaped jaw 738 movable between a first position in which the clamp portion 704 is open and a sleeve can be inserted laterally into the clamp portion, and a second position in which the clamp portion is closed and a sleeve can be laterally retained or captured within the clamp portion.

The ring-shaped portion 702 can define a central opening sized and configured to receive a first sleeve therethrough. The clamp portion 704 can define a central opening sized and configured to receive a second sleeve therethrough. Accordingly, the cap 700 can be used to selectively couple first and second sleeves to one another, thereby acting as a fulcrum for manipulation forces applied to the sleeves or to instruments inserted therethrough.

As described in further detail below, the fulcrum cap 700 can be used in conjunction with (e.g., can be coupled to a distal end of) a tool which can be manipulated by a user to move the C-shaped jaw 738 between the first open position and the second closed position to capture a sleeve in the clamp portion 704.

Figure 8:
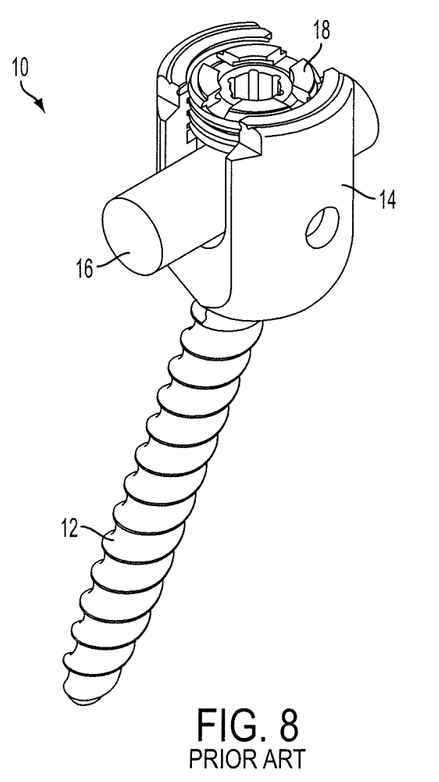
FIG. 8 is a perspective view of a prior art bone anchor assembly that includes a bone anchor and a receiver member having a spinal fixation element positioned therein.

FIG. 8 illustrates a prior art bone anchor assembly 10 that can be implanted in a bony structure of a patient (e.g., in a lateral mass or pedicle of the patient's spine). The bone anchor assembly 10 can include a bone anchor 12, a receiver member 14 for receiving a spinal fixation element, such as a spinal rod 16, to be coupled to the bone anchor 12, and a closure mechanism 18 to capture or lock the spinal fixation element within the receiver member 14 and fix the angular orientation of the bone anchor 12 relative to the receiver member 14. An access device (not shown), such as a percutaneous access device or extension, can be selectively or releasably coupled to the bone anchor assembly 10, e.g., such that a first end of the access device can be disposed adjacent to a vertebra while a second end of the access device extends above the patient's skin to a location outside of the patient. The access device can be integrally formed with the receiver member 14 or can be releasably or selectively attached to the receiver member 14. Exemplary percutaneous access devices are disclosed in U.S. application Ser. No. 13/625,034 filed on Sep. 24, 2012, and entitled "Devices and Methods for Positioning a Spinal Fixation Element," the entire disclosure which is hereby incorporated by reference herein.

Figure 9A:
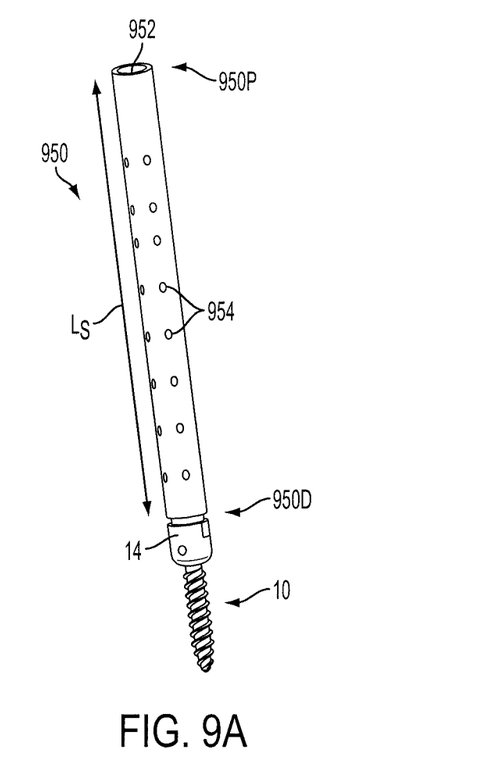
FIG. 9A is a perspective view of a sleeve coupled to the receiver member of FIG. 8.
Figure 9B:
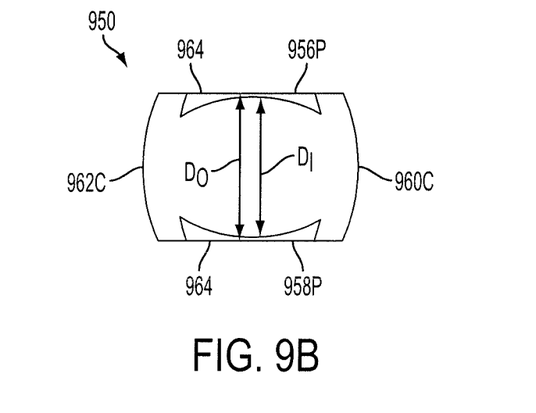
FIG. 9B is a top end view of the sleeve of FIG. 9A.

FIG. 9A illustrates an exemplary embodiment of a sleeve 950 for use with the fulcrum caps disclosed herein and the bone anchor assembly 10. The sleeve 950 can be configured to extend over a percutaneous access device to provide rigidity and allow a user to manipulate a bone anchor assembly 10 coupled to the access device without breaking off or otherwise detaching the percutaneous access device therefrom. The sleeve 950 can also be coupled to a bone anchor assembly without the presence of an access device, such that the sleeve itself acts as an access device. The sleeve 950 can have an elongate, at least partially cylindrical shape with proximal and distal ends 950P, 950D and an inner lumen 952 extending therebetween. An outer surface of the sleeve 950 can have a plurality of surface features, such as indentations 954, formed therein to facilitate gripping by a user's hand or by a distraction or compression tool. The sleeve 950 can have various lengths and diameters which can be selected for a particular surgical procedure, e.g., based on a particular patient's anatomy or the type of procedure being performed. In some embodiments, the sleeve 950 can have a length $L_S$ in the range about 100 mm to about 200 mm. In an exemplary embodiment, the length Ls is selected such that the sleeve extends above the patient's skin surface by an appreciable amount, e.g., about 145 mm to when the distal end of the sleeve is disposed adjacent to a bone surface. As shown in FIG. 9B, an inner diameter $D_I$ of the sleeve 950 can be in the range of about 11 mm to about 12 mm and an outer diameter $D_O$ of the sleeve 950 can be in the range about 12.5 mm to about 13.5 mm.

The distal end 950D of the sleeve 950 can be configured to mate with the receiver member 14 of a bone anchor assembly 10 or can be formed integrally therewith. For example, as shown in FIG. 9B, the sleeve 950 can include projections 964 configured to mate with corresponding grooves or indentations formed on an outer surface of a screw extension or receiver member. The distal end 950D of the sleeve can be tapered, and an outer diameter of the distal end 950D can be in the range about 11.5 mm to about 12.5 mm. An inner diameter of the tapered distal end 950D can be in the range about 11 mm to about 12 mm. In an exemplary embodiment, the lumen of the sleeve is not tapered and the inner diameter at the distal end 950D is approximately the same as the inner diameter $D_I$ of the sleeve 950 at its proximal end.

The proximal end 950P of the sleeve 950 can be configured to mate with or couple to any of the fulcrum caps disclosed herein. For example, the proximal end 950P of the sleeve 950 can include one or more mating features that correspond to a size and shape of a sleeve-receiving portion of a fulcrum cap (e.g., the ring-shaped member 202 of the fulcrum cap 200). In some embodiments, the proximal end 950P of the sleeve 950 can have first and second opposed planar exterior sides 956P, 958P and first and second curved exterior sides 960C, 962C. The first and second planar sides 956P, 958P can have various heights, but in a preferred embodiment extend along about 5% or about 8 mm of the length $L_S$ of the sleeve 950. A height of the planar sides 956P, 958P can also be less than or equal to the height $H_R$ of the ring-shaped member of a fulcrum cap such that when the proximal end 950P of the sleeve 950 is inserted into the ring-shaped member, the proximal end 950P of the sleeve 950 is flush or sub-flush with the proximal surface of the ring-shaped member. The planar sides 956P, 958P can prevent the sleeve from rotating relative to the fulcrum cap when the sleeve is inserted into a sleeve-receiving portion of the fulcrum cap.

The fulcrum caps disclosed herein can be used to facilitate various manipulations of sleeves, bone anchor assemblies, and/or vertebrae to which the sleeves or anchor assemblies are coupled. For example, methods of distracting, compressing, and/or derotating vertebrae using one or more fulcrum caps are provided. In the discussion below, one or more exemplary fulcrum caps are shown and described. It will be appreciated, however, that any of the fulcrum caps disclosed herein can be used in a similar fashion to distract, compress, and/or derotate vertebrae. In some embodiments, the methods described below can be performed by a user using only one hand.

In some embodiments, a bone anchor assembly 10 can be implanted in bone using various techniques. For example, a percutaneous access device can be used to provide a minimally-invasive approach to a pedicle or lateral mass of a vertebra. The bone surface can be prepared to receive the bone anchor assembly 10, generally by drilling a hole which is sized appropriately to receive the threaded shaft of the bone anchor 12 in an interference fit. The bone anchor 12 can be driven into the prepared hole using a driver tool fitted to the bone anchor 12. The bone anchor 12 can be attached to the receiver member 14 before or after the bone anchor 12 is inserted into bone. As noted above, an access device can be integrally formed with the receiver member 14 or can be selectively or releasably mated thereto. Any number of bone anchor assemblies 10 can be implanted in the patient's spine, in the same or in different vertebrae. A sleeve 950 can be attached to the receiver member 14 of each bone anchor assembly 10 or some other component of each bone anchor assembly, or can be disposed over an access device coupled to the bone anchor assembly. It will thus be appreciated that a plurality of bone anchor assemblies 10 can be implanted in the patient's spine, in adjacent or non-adjacent vertebrae, and each of the plurality of bone anchor assemblies 10 can have a sleeve extending proximally therefrom to a point external to the patient.

Figure 10A:
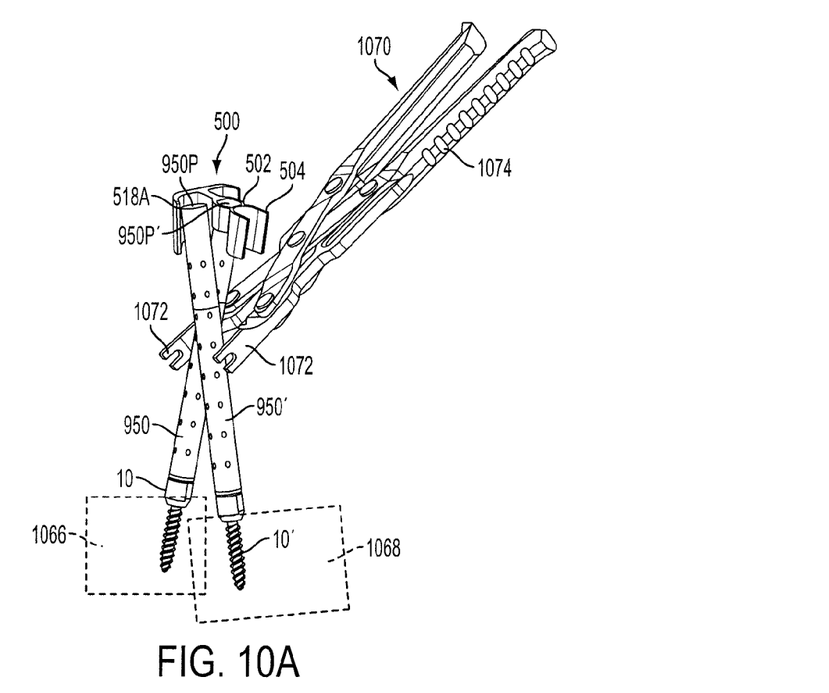
FIG. 10A is a perspective view of first and second sleeves having an exemplary fulcrum cap coupled thereto and being engaged by a compression tool.
Figure 10B:
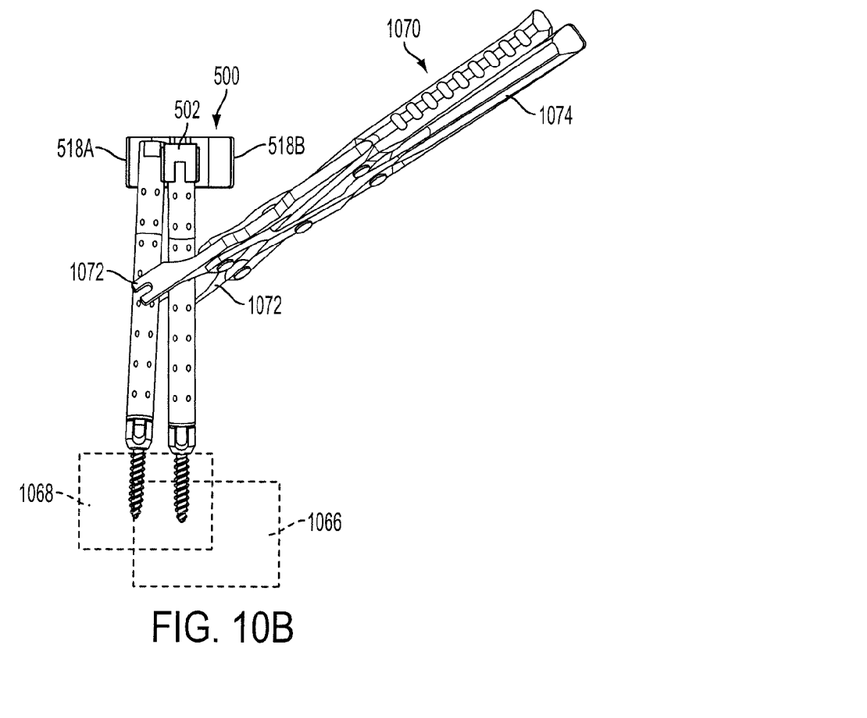
FIG. 10B is another perspective view of the first and second sleeves of FIG. 10A.

FIGS. 10A-10B illustrate an exemplary method of compressing and/or derotating first and second vertebrae 1066, 1068 using a fulcrum cap 500. As shown, a first bone anchor assembly 10 and a first sleeve 950 can be coupled to the first vertebra 1066. A second bone anchor assembly 10' and a second sleeve 950' can be coupled to the second vertebra 1068. The anatomical structure and the placement of the bone anchor assemblies can be such that the sleeves 950, 950' intersect or criss-cross at a point outside of the patient. In other embodiments, however, the sleeves can be non-intersecting such that they do not criss-cross. The proximal end 950P of the first sleeve 950 can be received in, coupled to, or supported by the first wing portion 518A of the fulcrum cap 500. The proximal end 950P' of the second sleeve 950' can be received in, coupled to, or supported by the ring-shaped member 502 of the fulcrum cap 500. It will be appreciated that the first and second sleeves 950, 950' can be received in, coupled to, or supported by any sleeve-receiving portion of the fulcrum cap, including the first and second wings 518A, 518B, the ring-shaped member 502, and the U-shaped extension 504.

After positioning the fulcrum cap 500 relative to the sleeves 950, 950' and/or coupling the sleeves 950, 950' to the fulcrum cap 500, any of a variety of compression tools known in the art can be used to apply a compressive force to the sleeves 950, 950' to compress the vertebrae 1066, 1068 toward one another. For example, a compression tool 1070 can include pivotable jaws 1072 coupled to a handle portion 1074 such that squeezing the handle portion is effective to squeeze the jaws 1072 towards one another. The jaws 1072 can be positioned to capture both sleeves 950, 950' and apply a compressive force thereto when the handle portion 1074 is actuated.

It will be appreciated that, when the sleeves 950, 950' are aligned along an axis that is parallel to a longitudinal axis of the patient's spine (or to a desired longitudinal axis), a compressive force applied thereto can effect purely compressive movement of the vertebrae 1066, 1068. If the sleeves 950, 950' are offset, such that they are aligned along an axis that is not parallel to the longitudinal axis of the patient's spine (or to a desired longitudinal axis), squeezing together the two sleeves 950, 950' can be effective to compress the vertebrae 1066, 1068 and/or to derotate the vertebrae 1066, 1068 (e.g., to rotate at least one vertebra with respect to at least one other vertebra about a longitudinal axis of the vertebra). In some embodiments, the jaws 1072 of the compression tool 1070 can be positioned adjacent to the patient's skin surface e.g., within about 5 mm of the patient's skin surface to maximize the amount of compression that is translated from the sleeves 950, 950' to the vertebrae 1066, 1068. While holding the vertebrae 1066, 1068 in a compressed and/or derotated position, a spinal fixation element, e.g., a spinal rod, can be secured to the bone anchor assemblies 10, 10' to maintain the vertebrae in the desired position after the compressive or derotative force is removed.

Figure 11:
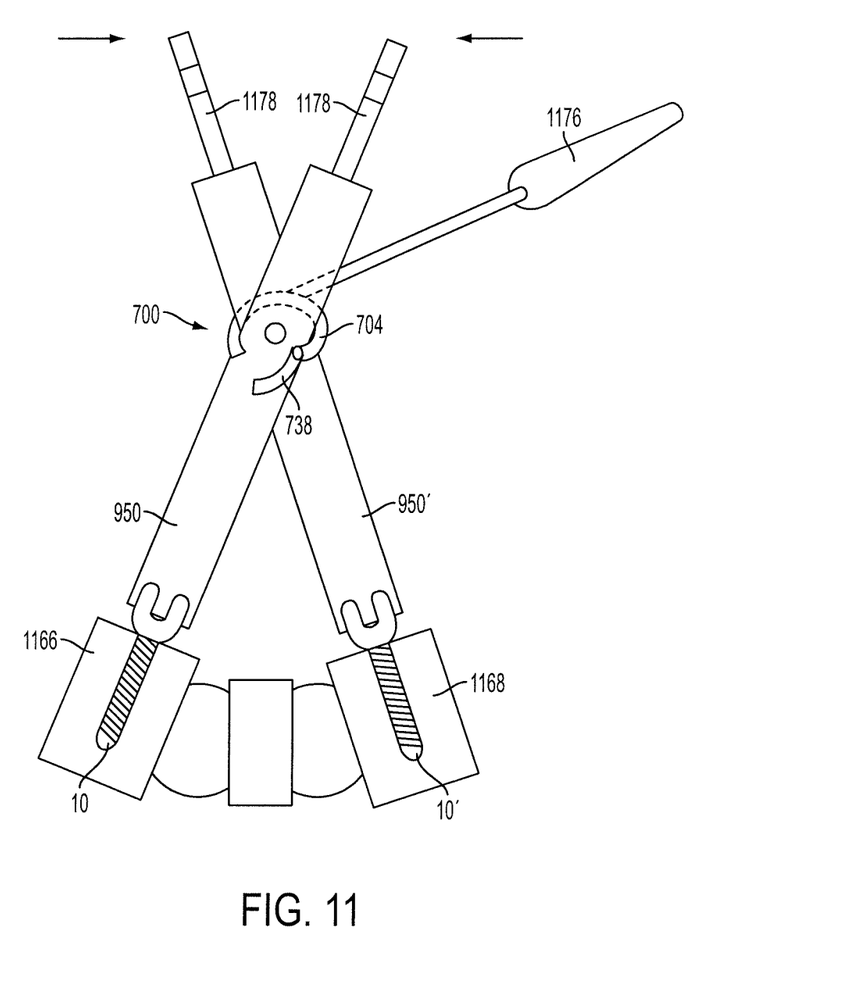
FIG. 11 is side view of the fulcrum cap of FIG. 7 coupled to first and second sleeves.

FIG. 11 illustrates another exemplary method of compressing and/or derotating vertebrae in which the fulcrum cap 700 is used. As shown, a first bone anchor assembly 10 can be implanted in a first vertebra 1166 and a first sleeve 950 can be coupled to the first bone anchor assembly. A second bone anchor assembly 10' can be coupled to a second vertebra 1168 and a second sleeve 950' can be coupled to the second bone anchor assembly.

As shown, the anatomical structure and the placement of the bone anchor assemblies can be such that the sleeves 950, 950' intersect or criss-cross at a point outside of the patient. In other embodiments, however, the sleeves can be non-intersecting such that they do not criss-cross. The first sleeve 950 can be received in, coupled to, or supported by the clamp portion 704 of the fulcrum cap 700. The second sleeve 950' can be received in, coupled to, or supported by the ring-shaped member (obscured from view in FIG. 11) of the fulcrum cap 700. In particular, the second sleeve 950' can be positioned in the clamp portion 704 and the C-shaped jaw 738 can be closed to capture the sleeve therein. A tool 1176 can be used to close the C-shaped jaw 738 and capture the sleeve 950'.

After positioning the fulcrum cap 700 relative to the sleeves 950, 950' and/or coupling the sleeves 950, 950' to the fulcrum cap 700, instruments 1178 inserted through the sleeves 950, 950' can be used to compress, distract, and/or derotate the vertebrae 1166, 1168, using the cap 700 as a fulcrum. For example, squeezing the instruments 1178 towards one another can be effective to compress the vertebrae 1166, 1168 and spreading the instruments 1178 apart can be effective to distract the vertebrae 1166, 1168. In addition, squeezing or spreading the instruments 1178 in a direction offset from the longitudinal axis of the patient's spine (or a desired longitudinal axis) can be effective to derotate the vertebrae 1166, 1168.

In some embodiments, the fulcrum cap 700 can be positioned at a distance away from the patient's skin surface, e.g., about 145 mm from the bone anchor, so as to maximize the mechanical advantage provided by the amount of compression applied to the sleeves when the cap 700 is coupled thereto. In some embodiments, with the fulcrum cap 700 so positioned, a compressive or distracting force can be applied to the sleeves at a location near the skin surface, such as adjacent to the skin surface. While holding the vertebrae 1166, 1168 in a compressed, distracted, and/or derotated position, a spinal fixation element, e.g., a spinal rod, can be secured to the bone anchor assemblies 10, 10' to maintain the vertebrae in the desired position after the compressive, distractive, and/or derotative force is removed.

Figure 12A:
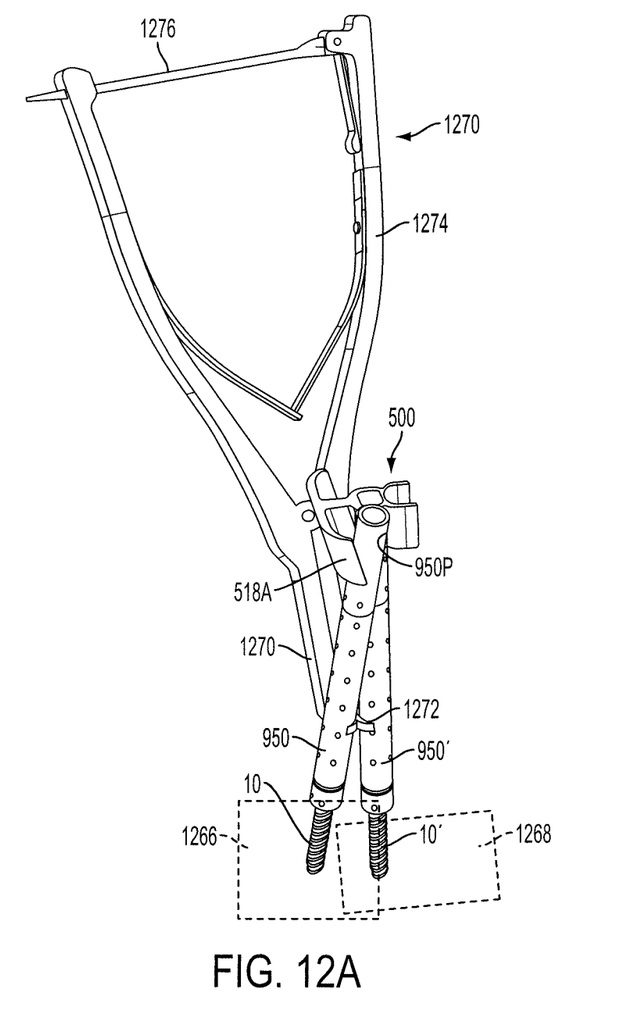
FIG. 12A is a perspective view of first and second sleeves in an intersecting or criss-crossed configuration and having a distraction tool and the fulcrum cap of FIG. 5 coupled thereto.
Figure 12B:
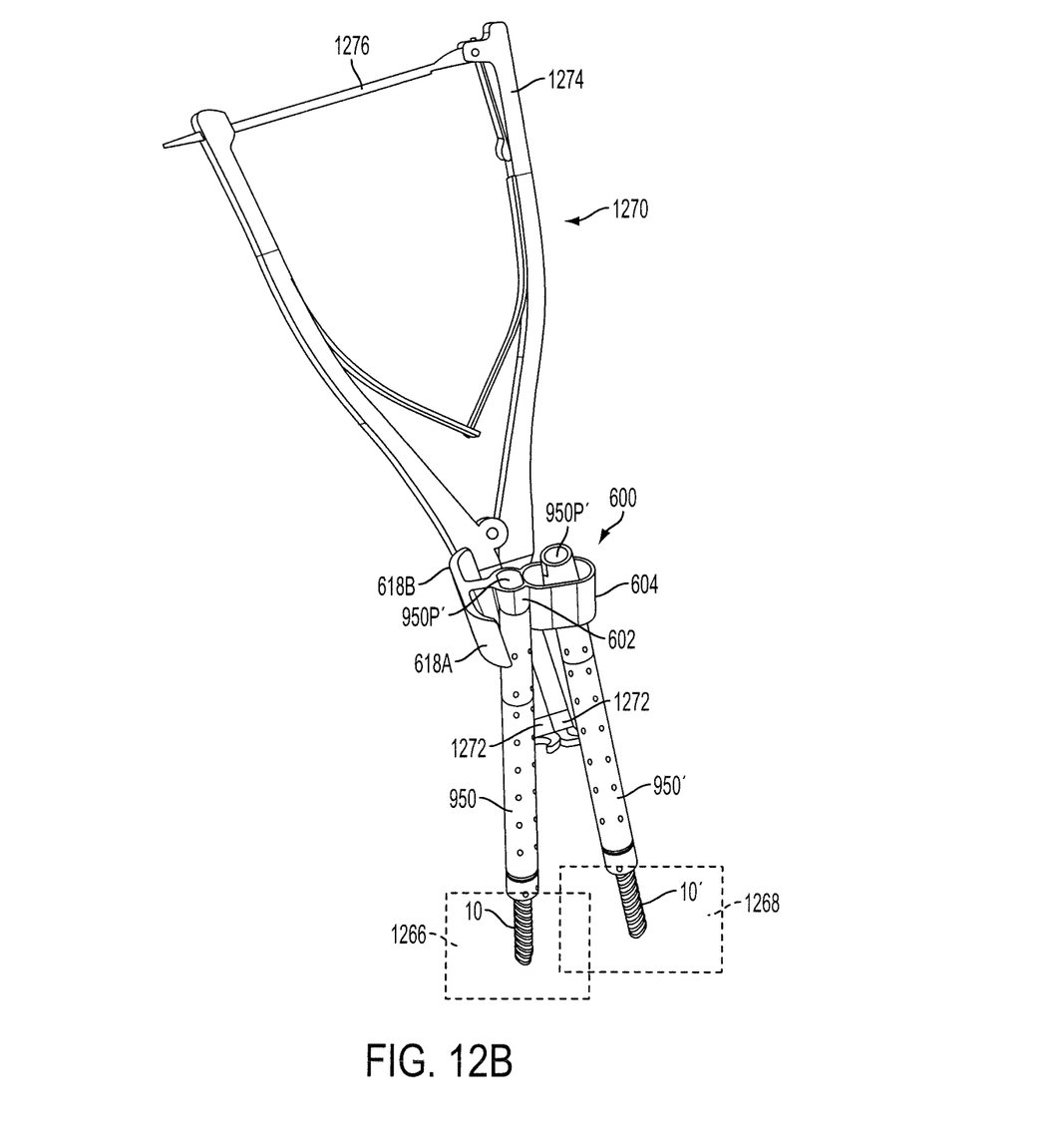
FIG. 12B is a perspective view of first and second sleeves in a longitudinally-aligned configuration and having a distraction tool and the fulcrum cap of FIG. 6 coupled thereto.

FIGS. 12A and 12B illustrate exemplary methods of manipulating vertebrae using the fulcrum cap 500 and the fulcrum cap 600, respectively. The method of FIG. 12A is similar to that of FIGS. 10A-10B, except that a distraction tool 1270 is used in place of the compression tool 1070. In particular, first and second spreadable jaws 1272 of the distraction tool can be positioned between the sleeves 950, 950' in engagement therewith. Squeezing a handle portion 1274 of the distraction tool 1070 can cause the jaws 1272 to spread apart, thereby distracting and/or derotating the sleeves 950, 950' and the vertebrae 1266, 1268 coupled thereto. It will be appreciated that the fulcrum cap 500 provides a mechanical advantage in applying the distraction/derotation force. Because the proximal end 950P of the first sleeve 950 is not fixed to the fulcrum cap 500, but rather just bears against the first wing 518A, the first sleeve 950 has a greater degree of freedom to move relative to the cap 500 than the second sleeve 950'. As shown, the distraction tool 1270 can include a ratcheting mechanism 1276 configured to fix a distance between the jaws 1272 to maintain the vertebrae in a distracted and/or derotated position until a spinal fixation element, e.g., a spinal rod, is secured to the first and second bone anchor assemblies 10, 10'.

The method of FIG. 12B is similar to that of FIG. 12A, except that the fulcrum cap 600 is used to provide freedom of movement for the proximal end 950P' of the second sleeve 950'. In particular, the proximal end 950P' of the second sleeve 950' can be received in the closed receiver 604 of the fulcrum cap 600. The proximal end 950P of the first sleeve 950 can be received in the ring-shaped member 602 of the fulcrum cap 600. It will be appreciated that the first and second sleeves 950, 950' can be received in, coupled to, or supported by any sleeve-receiving portion of the fulcrum cap, including the first and second wings 618A, 618B, the ring-shaped member 602, and the closed receiver 604. Because the proximal end 950P' of the second sleeve 950' is not fixed to the fulcrum cap 600, but rather is free to move slightly within the closed receiver 604, the second sleeve 950' has a greater degree of freedom to move relative to the cap 600 than the first sleeve 950. A distraction tool 1270 can be used as described above to distract and/or derotate the vertebrae 1266, 1268 using the fulcrum cap 600 to provide a mechanical advantage.

The methods described herein can be performed on any number of vertebrae at any level in a spine to distract, compress, and/or derotate the vertebrae. Once the vertebrae are positioned as desired, the bone anchor assemblies implanted therein can be secured to a spinal fixation element to maintain the desired positioning of the vertebrae. For example, a spinal fixation element can be inserted through one or more receiver members and can be reduced using known devices and techniques. A closure mechanism, such as a single or dual closure mechanism, can be inserted into the receiver member and engaged with the receiver member to angularly fix the receiver member relative to the bone anchor and secure the fixation element thereto.

As will be appreciated by a person skilled in the art, the devices and methods disclosed herein can be used to treat a variety of conditions of spinal deformities, such as scoliosis. One exemplary method for treating scoliosis includes vertebral body derotation (VBD), which involves sequentially derotating the vertebrae at each level, starting from a neutral inferior vertebra, such that the vertebrae lie in a neutral plane. In certain aspects, the derotation steps can be performed after the rods are reduced in the receiver members, but before the closure mechanisms are attached to the receiver members.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A spinal instrumentation kit, comprising:
   a first bone anchor configured to be implanted in a first vertebra;
   a first elongate body configured to couple to the first bone anchor;
   a second bone anchor configured to be implanted in a second vertebra;
   a second elongate body configured to couple to the second bone anchor; and
   a connector having a ring-shaped member and a U-shaped extension, the ring-shaped member being configured to slidably receive one of the first and second elongate bodies and to prevent the one of the first and second elongate bodies from rotating relative to the ring-shaped member, and the U-shaped extension having first and second arms each having a free end, the free ends forming an open end of the U-shaped extension that faces away from the ring-shaped member, the U-shaped extension allowing the other one of the first and second elongate bodies to rotate and pivot freely toward and away from the ring-shaped member;

wherein when the first and second bone anchors are implanted in first and second vertebrae and the first and second elongate bodies are coupled to the first and second bone anchors, the connector is configured to function as a fulcrum to allow pivotal movement of the first and second elongate bodies about the fulcrum to thereby compress or distract the first and second vertebrae relative to one another.

2. The kit of claim 1, wherein the connector includes an adjustable rack configured to adjust the distance between the U-shaped extension and the ring-shaped member.

3. The kit of claim 1, wherein the ring-shaped member is configured to receive a proximal end of the first elongate body therein.

4. The kit of claim 3, wherein an inner surface of the ring-shaped member has a shape that is complementary to a shape of the proximal end of the first elongate body.

5. The kit of claim 4, wherein the inner surface of the ring-shaped member forms an interference fit with the proximal end of the first elongate body.

6. The kit of claim 3, wherein when the proximal end of the first elongate body is received in the ring-shaped member, a proximal surface of the first elongate body is flush or sub-flush with a proximal surface of the ring-shaped member.

7. The kit of claim 1, further comprising first and second support arms extending from the ring-shaped member, the first and second support arms each being configured to seat one of the first and second elongate bodies.

8. The kit of claim 1, wherein the ring-shaped member has a first height and the U-shaped extension has a second height that is greater than the first height.

9. The kit of claim 1, wherein the first and second elongate bodies comprise first and second sleeves, each of the first and second sleeves having an inner lumen extending therethrough for providing a pathway through tissue.

10. The kit of claim 1, wherein an inner surface of the U-shaped extension is configured so that a proximal end of one of the first and second elongate bodies can be seated thereagainst.

11. The kit of claim 1, wherein the ring-shaped member and the U-shaped extension are integrally formed.

12. A spinal instrumentation kit, comprising:
a first bone anchor configured to be implanted in a first vertebra;
a first sleeve configured to couple to the first bone anchor;
a second bone anchor configured to be implanted in a second vertebra;
a second sleeve configured to couple to the second bone anchor; and
a connector having a ring-shaped member configured to slidably receive a first end of the first sleeve and to prevent the first sleeve from rotating relative thereto and a hemi-cylindrical shaped extension configured to seat a first end of the second sleeve and to allow the first end of the second sleeve to rotate and pivot relative thereto, a superior surface of the ring-shaped member being flush with a superior surface of the hemi-cylindrical shaped extension;

wherein when the first and second bone anchors are implanted in first and second vertebrae and the first and second elongate sleeves are coupled to the first and second bone anchors, the connector is configured to function as a fulcrum to allow the first and second elongate sleeves to pivot about the fulcrum to thereby compress, distract, or derotate the first and second vertebrae relative to one another.

13. The kit of claim 12, wherein the ring-shaped member is configured to receive a proximal end of the first elongate body therein.

14. The kit of claim 12, wherein an inner surface of the ring-shaped member has a shape that is complementary to a shape of the proximal end of the first elongate body.

15. The kit of claim 14, wherein the inner surface of the ring-shaped member is shaped so as to provide an interference fit with the proximal end of the first elongate body.

16. The kit of claim 12, wherein the ring-shaped member has a first height and the hemi-cylindrical extension has a second height that is greater than the first height.

17. The kit of claim 12, wherein the ring-shaped member and the hemi-cylindrical extension are integrally formed.

* * * * *